(12) United States Patent
Minoz et al.

(10) Patent No.: US 11,596,809 B2
(45) Date of Patent: Mar. 7, 2023

(54) INDICATOR ARRANGEMENTS AND METHODS FOR SUCH ARRANGEMENTS

(71) Applicant: Elekta Ltd., Crawley (GB)

(72) Inventors: Alain Minoz, Bromma (SE); Kjell Eldered, Salstjö-Duvnäs (SE)

(73) Assignee: ELEKTA LTD.

( * ) Notice: Subject to any disclaimer, the term of this patent is extended or adjusted under 35 U.S.C. 154(b) by 303 days.

(21) Appl. No.: 16/754,506

(22) PCT Filed: Nov. 1, 2017

(86) PCT No.: PCT/EP2017/077982
§ 371 (c)(1),
(2) Date: Apr. 8, 2020

(87) PCT Pub. No.: WO2019/086111
PCT Pub. Date: May 9, 2019

(65) Prior Publication Data
US 2020/0346039 A1    Nov. 5, 2020

(51) Int. Cl.
*A61N 5/10* (2006.01)
*G01R 33/28* (2006.01)
*G01R 33/30* (2006.01)

(52) U.S. Cl.
CPC .......... *A61N 5/1049* (2013.01); *G01R 33/283* (2013.01); *G01R 33/307* (2013.01);
(Continued)

(58) Field of Classification Search
CPC ............... A61N 5/10; A61N 5/1049; A61N 2005/1063; A61N 2005/1051;
(Continued)

(56) References Cited

U.S. PATENT DOCUMENTS 5,066,915 A    11/1991  Omori et al.
7,852,080 B2 *  12/2010  Takamori ............... G01R 33/28
                                                   324/318
(Continued)

FOREIGN PATENT DOCUMENTS

EP     2 881 033 A1   10/2015
WO  WO 2006/126108 A1   11/2006

OTHER PUBLICATIONS

International Search Report, Application No. PCT/EP2017/077982, dated Jul. 10, 2018, European Patent Office, Rijswijk, Netherlands.

*Primary Examiner* — Jurie Yun
(74) *Attorney, Agent, or Firm* — Burr & Forman LLP; Jeffrey H. Kamenetsky

(57) ABSTRACT

The invention relates to a position indicator for a system for moving a patient in a non-invasive therapy system, wherein the system for moving includes a patient support arranged outside a treatment space of a medical apparatus of the non-invasive therapy system, a treatment table arranged inside the treatment space in the medical apparatus, and a patient bed movable in a longitudinal direction from the patient support to the treatment table and back by means of activation of a transferring mechanism, wherein the position indicator comprises a number of light emitting elements arranged in the patient support and each being arranged to receive activation signals instructing a receiving light emitting element to emit light to indicate positions for treatment equipment.

17 Claims, 5 Drawing Sheets

(52) U.S. Cl.
CPC ............... *A61N 2005/1051* (2013.01); *A61N 2005/1055* (2013.01); *A61N 2005/1063* (2013.01)

(58) Field of Classification Search
CPC ............ A61N 2005/1055; G01R 33/30; G01R 33/28; G01R 33/307; G01R 33/283; A61B 5/055; A61B 6/0407; A61B 6/0492; A61G 13/02; A61G 2210/50
See application file for complete search history.

(56) References Cited

U.S. PATENT DOCUMENTS

| | | | |
|---|---|---|---|
| 9,078,628 B2 * | 7/2015 | Cumpson | A61B 5/704 |
| 2008/0204017 A1 | 8/2008 | Takamori et al. | |
| 2012/0126815 A1 | 5/2012 | Hahn | |
| 2015/0150740 A1 * | 6/2015 | Lewald | A61B 6/0407 5/601 |

* cited by examiner

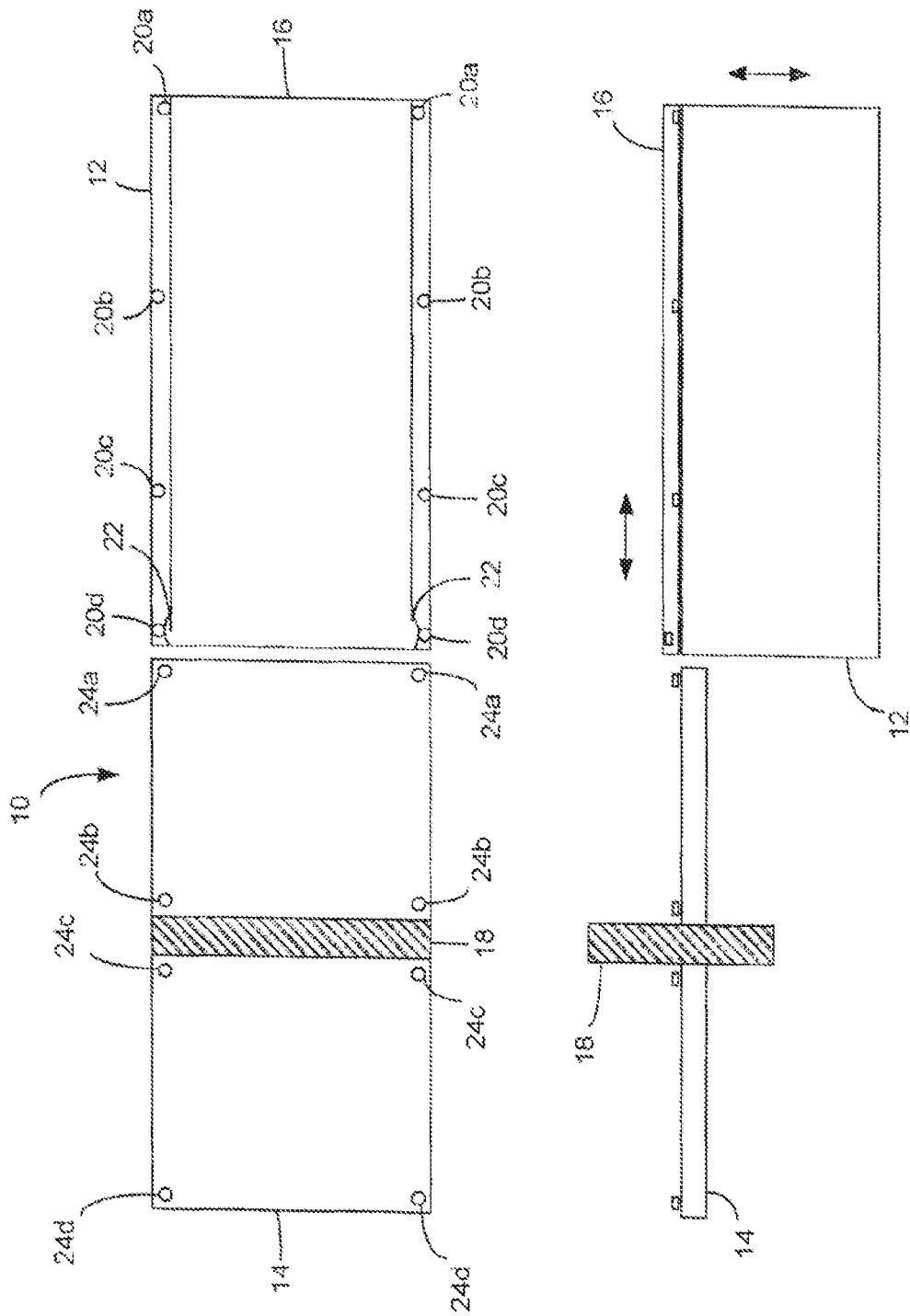

INDICATOR ARRANGEMENTS AND METHODS FOR SUCH ARRANGEMENTS

TECHNICAL FIELD

The present invention relates to medical devices, and particularly to systems and devices for moving a patient to and from a magnetic resonance imaging system or a combined magnetic resonance imaging and radiotherapy system.

BACKGROUND

In medical non-invasive therapy systems, in particular radiotherapy systems, such as conventional linear accelerators or MR Linac systems, the patient anatomy being treated or imaged should be aligned with the radiation isocentre as accurate as possible for each and every set up and each treatment fraction. One source of potential inaccuracy in the alignment is the repositioning of the bed on which the patient rests. As many medical systems require the patient to be placed into an enclosed and confined space, hereinafter called treatment bore, the patient must be set up for treatment outside the treatment bore and then transported into the treatment bore for the medical treatment to begin. Therefore, the bed must be movable between these two locations to a high degree of accuracy as misalignments during set up may entail that the patient will need to be removed from the medical radiotherapy system and realigned before treatment can commence, and thus wasting time and resources.

It is also of importance that the patient positioning is as stable as possible during the movement as well during the treatment or imaging. Hence, the position of the bed in treatment bore in the medical radiotherapy system must be very stable. The process of moving the bed from its support outside the medical radiotherapy system into the treatment bore inside the medical radiotherapy system itself requires careful alignment with the treatment table of the system as well as high degree of stability.

Furthermore, it is also important that the process for patient set up and of moving the bed from its support outside the medical radiotherapy system into the treatment space inside the medical radiotherapy system is secure for the patient and easy to handle for the medical staff. The risk of patient injuries must be minimized during movement as well as during treatment in order to provide as high patient security as possible and minimize risk for patient movements during treatment.

Moreover, in medical non-invasive therapy systems, in particular in MR Linac systems, it is of very high importance that all material in the treatment bore or treatment volume is known and taken into account in the planning system. As all material will absorb radiation dose, it is important to reduce the material present in the treatment bore as much as possible and it is also important that the positions of material structures are known.

It is of further importance that equipment having a position relatively the patient such as the coil frame as well as patient supporting structures including head support and support for the feet are positioned accurately on the table-top or patient support. The operator must install the coil frame on table-top at a certain position and there may be around 100 different positions. This is usually performed manually, which is time-consuming and may entail positioning errors.

Due to the delivered radiation and performed imaging inside the bore, no electronic equipment can be used in the table-top for indicating the position of, for example, the coil frame on the table-top. On one hand, the imaging will most likely be influenced and disturbed and, on the other hand, the radiation will likely shorten lifespan of and/or destroy the electronic equipment.

In summary, there are several important factors to consider when designing a movable bed and treatment table for use in medical radiotherapy systems, such as MR Linac systems. It is of importance to make sure that the equipment such as the coil frame, as well as the patient, is positioned very accurately. The accuracy requires a very reliable positioning of the coil frame and the patient on the patient bed. In addition, there is a need for providing good quality imaging when tracking the patient. When using magnetic resonance imaging systems for this it is thus important to position the coil in a stable and accurate position while at the same time ensuring a good and efficient handling of the system during set up.

SUMMARY OF THE INVENTION

An object of the present invention is to provide a user and patient friendly movable bed and treatment table for use in medical radiotherapy systems, such as MR Linac systems.

Another object is to provide a more efficient handling of a medical radiotherapy systems, such as MR Linac system, during set up These and other objects are fulfilled by the present invention as defined by the independent claims. Preferred embodiments are defined by the dependent claims.

Non-invasive therapy systems may refer to a medical apparatus and include at least a magnetic resonance imaging system or a radiotherapy system or any combination thereof.

According to an aspect of the present invention, there is a provided a position indicator for a system for moving a patient in a non-invasive therapy system, wherein the system for moving includes a patient support arranged outside a treatment space of a medical apparatus of the non-invasive therapy system, a treatment table arranged inside the treatment space in the medical apparatus, and a patient bed movable in a longitudinal direction from the patient support to the treatment table and back by means of activation of a transferring mechanism, wherein the position indicator comprises a number of light emitting elements arranged in the patient support and each being arranged to receive activation signals instructing a receiving light emitting element to emit light to indicate positions for treatment equipment.

In embodiments of the present invention, the light emitting elements are arranged to receive activation signals instructing a receiving light emitting element to emit light to indicate positions, in a longitudinal direction, where the treatment equipment is to be positioned at the patient support.

According to another embodiment of the present invention, the patient support is provided with a number of position markers and the position indicator comprises at least one light emitting element arranged at each position marker, wherein a position marker is lit up when a corresponding light emitting element is instructed to emit light.

In other embodiments of the present invention, the position markers include a transparent or semi-transparent material and are arranged on a longitudinal edge part of the patient support and wherein the light emitting elements are arranged to individually emit light towards a respective position marker.

Further embodiments of the present invention comprise position markers including a transparent or semi-transparent material and wherein the light emitting elements are arranged to emit light towards a respective position marker.

According to embodiments of the present invention, the light emitting elements are arranged in an upper surface of the patient support.

In accordance with other embodiments of the present invention, the light emitting elements are arranged in a guide rail of the patient support.

In embodiments of the present invention, the light emitting elements are arranged to, upon receiving activation signals, emit light according to a predetermined sequence and/or color.

In embodiments of the present invention, the treatment equipment includes a coil arrangement including an anterior coil and a support stand, the support stand resting on the patient bed adjacent to longitudinal edges of the patient bed and being slidable along the patient bed in a longitudinal direction, wherein the light emitting elements are arranged to receive activation signals instructing a receiving light emitting element to emit light to indicate positions where the coil arrangement should be positioned at along the patient support.

According to embodiments of the present invention, the treatment equipment includes patient positioning devices arranged to be positioned at the patient support, wherein the light emitting elements are arranged to receive activation signals instructing a receiving light emitting element to emit light to indicate positions, in a longitudinal direction, where the patient positioning device should be positioned at the patient support.

In embodiments of the present invention, the light emitting elements are arranged to, upon receiving activation signals, to emit light according to a predetermined sequence and/or color, wherein a certain predetermined sequence and/or color is associated with a certain treatment equipment.

According to a further aspect of the present invention, there is provided a method for indicating a position in a system for moving a patient in a non-invasive therapy system, wherein the system for moving includes a patient support arranged outside a treatment space of a medical apparatus of the non-invasive therapy system, a treatment table arranged inside the treatment space in the medical apparatus, a patient bed movable in a longitudinal direction from the patient support to the treatment table and back by means of activation of a transferring mechanism, wherein the method comprises activating a position indicator comprising a number of light emitting elements arranged in the patient support, each being arranged to receive activation signals instructing a receiving light emitting element to emit light to indicate positions for treatment equipment.

According to embodiments of the present invention, the method further includes activating a position indicator comprising a number of light emitting elements arranged in the patient support, each being arranged to receive activation signals instructing a receiving light emitting element to emit light to indicate positions, in a longitudinal direction, where the treatment equipment it to be positioned at the patient support.

In embodiments of the present invention, the patient support is provided with a number of position markers and the position indicator comprises at least one light emitting element arranged at each position marker, wherein the method comprises lightening up a position marker by instructing a corresponding light emitting element to emit light.

Further embodiments of the present invention comprise position markers provided with a transparent or semi-transparent material and are arranged on a longitudinal edge part of the patient support, wherein the method comprises individually emitting light towards a position marker from a corresponding light emitting element.

In accordance with embodiments of the present invention, the method further comprises providing activation signals to instruct the light emitting elements to emit light according to a predetermined sequence and/or color.

According to embodiments of the present invention, the treatment equipment includes a coil arrangement including an anterior coil and a support stand, the support stand resting on the patient bed adjacent to longitudinal edges of the patient bed and being slidable along the patient bed in a longitudinal direction, wherein the method further comprises providing an activation signal to the light emitting elements instructing a receiving light emitting element to emit light to indicate positions, in a longitudinal direction, where the coil arrangement is to be positioned at the patient support.

In embodiments of the present invention, the treatment equipment includes patient positioning devices arranged to be positioned at the patient support, further comprising providing activation signals to the light emitting elements instructing a receiving light emitting element to emit light to indicate positions, in a longitudinal direction, where the patient positioning device is to be positioned at the patient support.

According to embodiments of the present invention, the method further comprises providing activation signals to the light emitting elements instructing a light emitting element to emit light according to a predetermined sequence and/or color, wherein a certain predetermined sequence and/or color is associated with a certain treatment equipment.

Preferred embodiments of the invention will now be described in relation to the drawings.

BRIEF DESCRIPTION OF THE DRAWINGS

For a better understanding of the present invention, and to show more clearly how it may be carried into effect, reference will now be made, by way of example, to the following drawings, in which:

FIG. 1 shows a plan view of a system in which the present invention can be used;

FIG. 2 shows a side view of the system in which the present invention can be used;

DESCRIPTION

Figure 3:
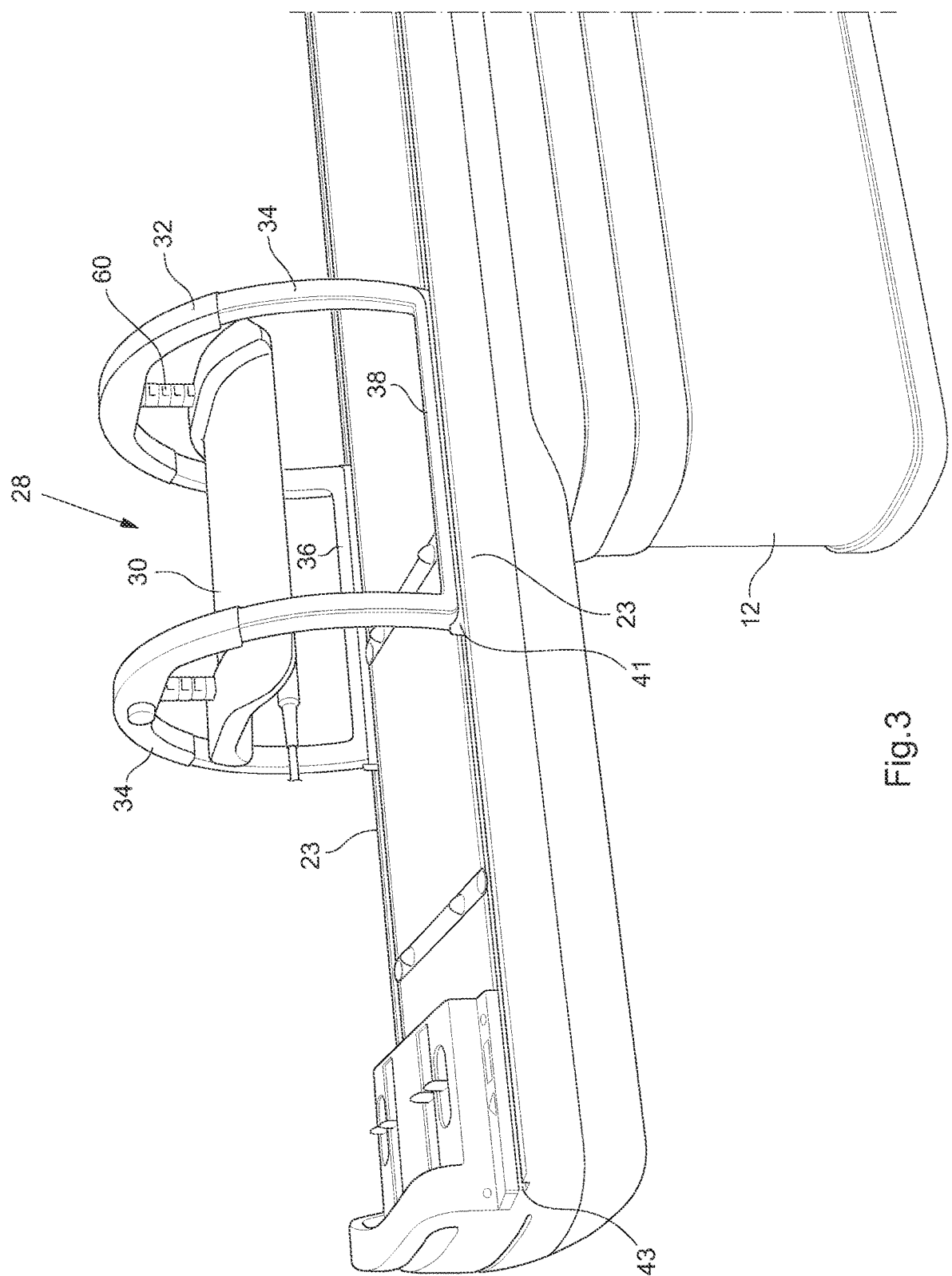
FIG. 3 shows a perspective view of the system in which the present invention can be used.

With reference first to FIGS. 1-3, a system in which the present invention can be used will be described. FIG. 1 shows a plan view of a system 10 and FIG. 2 shows a side view of the system of FIG. 1. The system 10 comprises a patient support 12, a treatment table 14, and a bed 16 which is movable between the patient support 12 and the treatment table 14. The treatment table 14 is schematically shown in FIGS. 1 and 2 and may form part of any medical treatment system but is particularly suitable for use in MR Linac radiotherapy systems. Hence, in embodiments of the present invention, the system 10 is arranged at a MR Linac radiotherapy system having radiation heads and radiation sources for generating beams of therapeutic radiation emanating from the radiation heads. One or more collimating elements (e.g. a Multi-leaf collimator in the Linac part) are provided for shaping the beam to conform to a desired cross-section. The radiation heads may be mounted on a rotatable gantry and controlled to rotate around the patient while directing the radiation towards the axis of rotation and the target within the patient. The target thus receives radiation from multiple angles and a higher dose than the surrounding healthy tissue. The extent of the treatment area 18, i.e., the volume in which the radiation beam operates, is illustrated schematically in FIGS. 1 and 2.

The patient support 12 may comprise a mechanism for altering the height of the support, for example, between a first height and second height. For example, the first (lower) height may be at a level suitable to allow the patient to climb on to the bed 16, while the second (higher) height is a level equal to the height of the treatment table 14 and allows the bed 16 to move between the support 12 and the treatment table 14.

The bed 12 may be moved in a direction along its longitudinal axis between the support 12 and the treatment table 14 in a manner to be described in more detail below. Those skilled in the art will appreciate that any suitable mechanism may be used for moving the bed 16. For example, the bed 16 may be moved by a pulley/belt system, a rack and pinion system, a conveyor belt, etc.

As described above, it is important that the bed can be smoothly transferred or moved between the support 12 and the treatment table 14 so that once on the table 14 the bed is correctly aligned within the system, which in many radiotherapy systems is crucial. In order to ensure that the bed 16 is correctly aligned during initial set-up and treatment, the system 10 may comprise guide elements 20a, 20b, 20c, 20d, arranged on an upper surface of the support 12. Alternatively, guide tracks may be arranged on an upper surface of the support 12 and treatment table 14 and corresponding guide rails may be arranged on the patient bed 16 such that the bed 16 can slide seamlessly between the support and the table.

In the illustrated embodiment, the patient support comprises four pairs of guide elements. However, fewer or more guide pairs may be provided without departing from the scope of the invention. The guide pairs may be uniformly spaced along the edges of the support 12 so as to prevent the bed 16 from moving significantly in the lateral direction (i.e., up and down the page in FIG. 1, and FIG. 2).

In the embodiment illustrated in FIGS. 1 and 2, the guide elements are rollers which move over the edge of the bed 16 as the bed is moved in the direction along its longitudinal axis. However, those skilled in the art will appreciate that any suitable guiding element which provides a low friction surface along which the bed can travel without sticking may be provided as an alternative. Further, guides need not be identical, and a mix of different guides may be provided in the same system without departing from the scope of the invention.

The treatment table 14 may comprise a plurality of guide elements 24a, 24b, 24c, 24d, on an upper surface of the table, similar to the guide elements on the support 12.

With reference now to FIG. 3, a treatment equipment, such as a MR coil arrangement, arranged at the system 10 will be described. The MR coil arrangement 28 includes an anterior coil 30 and a support stand 32 is arranged to be slidable along the patient bed 16 in a longitudinal direction when a patient is placed on the bed 16. The support stand 32 rests on the patient bed 16 and is arranged adjacent to longitudinal edges 23 of the patient bed 16 and include rails 41 being arranged to be slidable in grooves or guide tracks 43 provided in the patient bed 16. The coil arrangement 28 may further comprise a height adjustment mechanism 60 for adjusting the height of the anterior coil 30 above the patient bed 16. The height adjustment mechanism 60 may enable an operator to adjust the height of the anterior coil 16 parallel to a plane defined by the patient bed 16 as indicated in FIG. 3 or it may enable an operator to adjust the anterior coil 16 in an oblique manner (not shown) as seen in relation to the plane defined by the patient bed 16.

Figure 4:
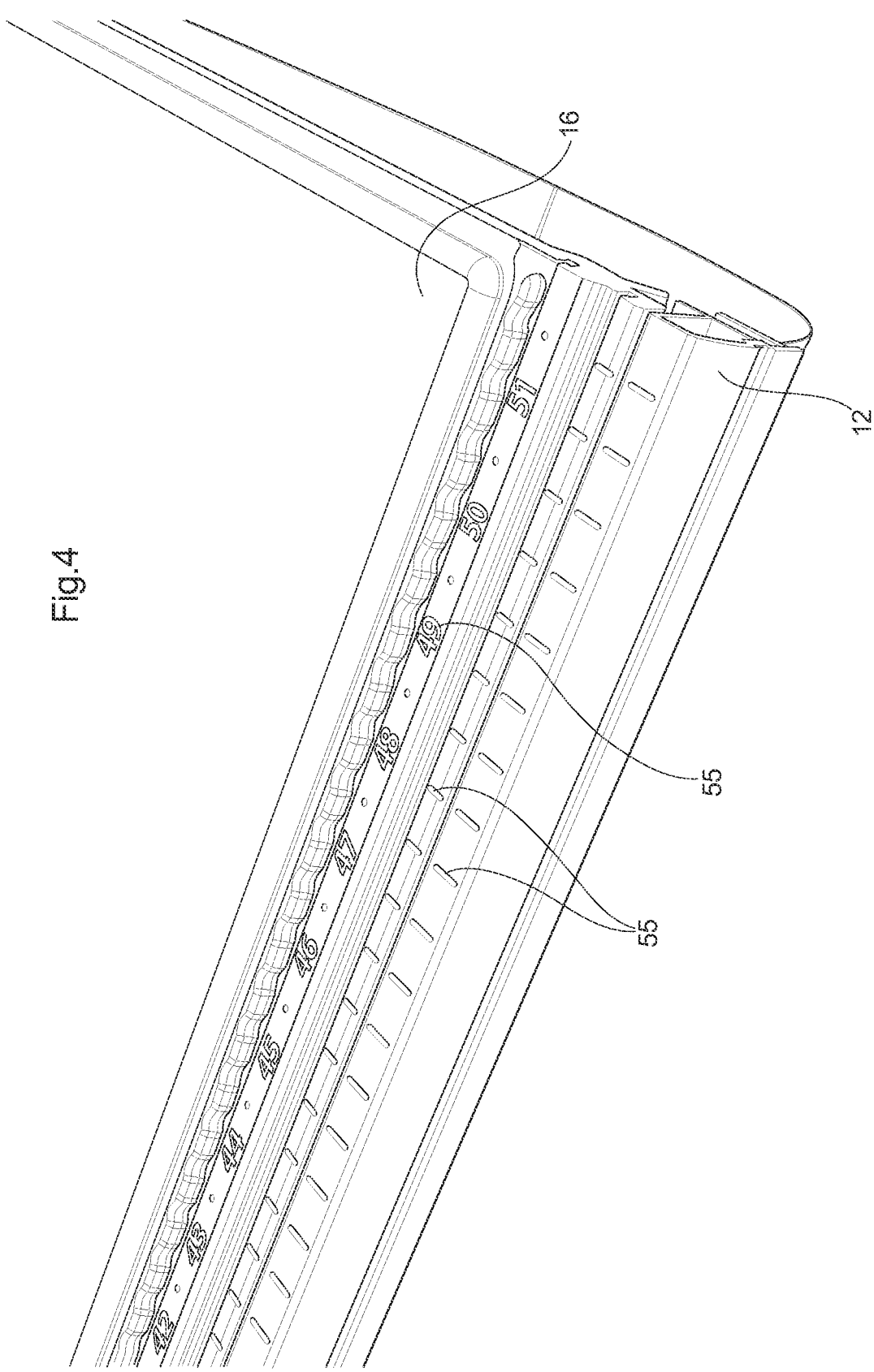
FIG. 4 shows a detailed view of the system shown in FIG. 3.
Figure 5:
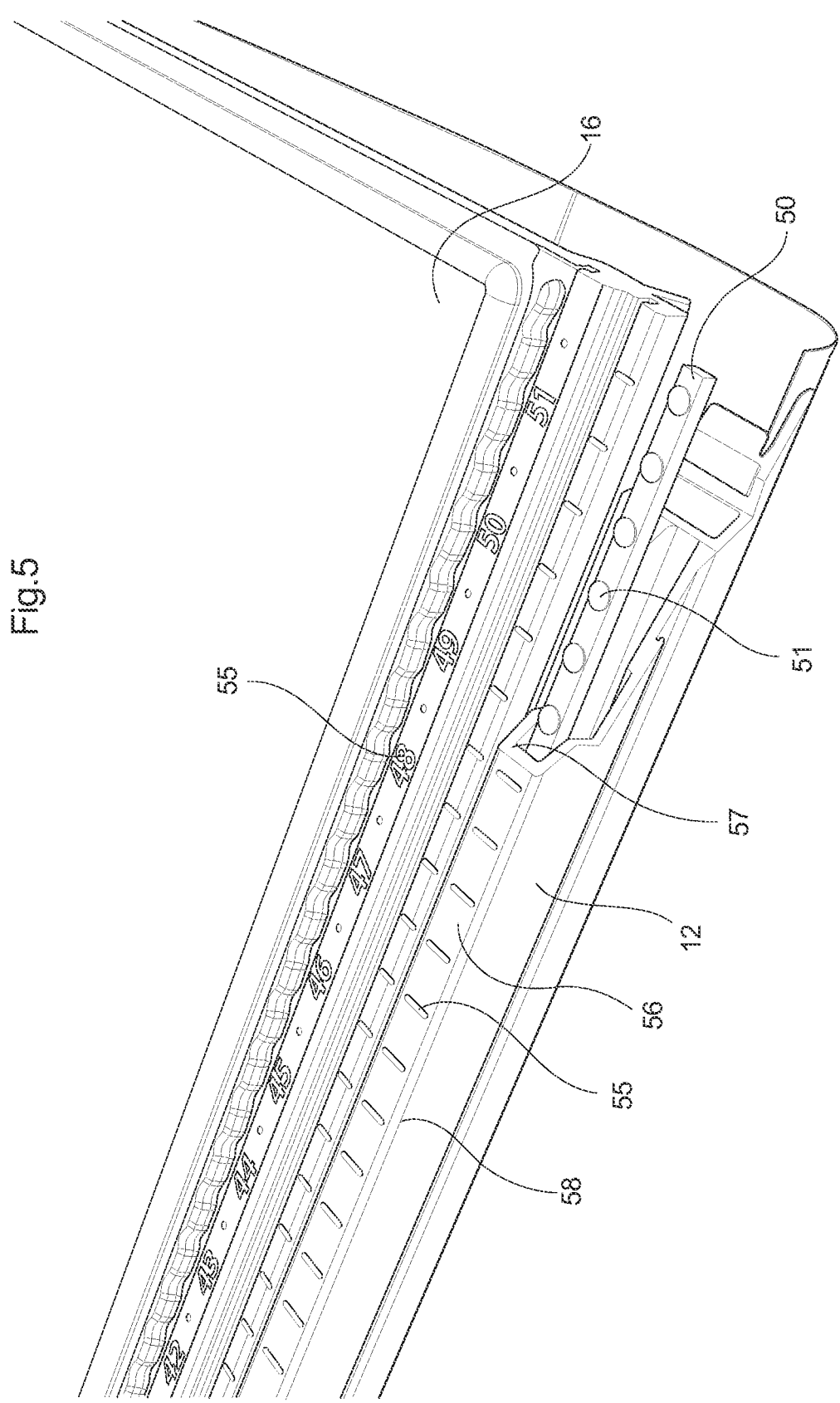
FIG. 5 shows a detailed view of a of an embodiment of the present invention.

FIGS. 4 and 5 shows more detailed views of the patient support 12 and the patient bed 16. Position markers 55 are provided on the patient bed 16 arranged as numbers along an edge of the patient bed 16. In this embodiment, a position indicator 50 is arranged as an array of light emitting elements 51, in this example light emitting diodes, on upper surface 56 of the patient support 12. The array of light emitting elements 51 is arranged such that each light emitting element is in line with a corresponding position marker 55 on the patient bed 16 when the bed 16 is placed in an end position or home position outside the treatment area 18 (see FIG. 3). According to an embodiment, shown in FIG. 5, the light emitting elements 51 are arranged beneath an edge part 57 shaped as a hollow elongated part along longitudinal direction of the patient support 12. The edge part 57 includes transparent areas 58, each being aligned with a corresponding position marker 55 and a corresponding light emitting element 51, when the patient bed is placed in the end position. The light emitting elements 51 are each arranged to receive activation signals instructing a receiving light emitting element 51 to emit light to indicate a position of, for example, the coil arrangement 28. However, other parts such as a head pillow, neck support, feet support for the patient may also be indicated by the light emitting elements 51.

In embodiments, the light emitting elements 51 are arranged to upon receiving activation signals to emit light according to a predetermined sequence and/or color. Thereby, for example, the position of a certain treatment equipment such as the coil arrangement or patient position device, e.g., feet, knee or neck support devices, can be indicated by a light emitting element 51 emitting light according to a first specific sequence and/or color, a position of a neck support with another light emitting element 51 emitting light according to a second specific sequence and/or color, and a position of a feet support with yet another light emitting element 51 emitting light according to a third specific sequence and/or color.

In embodiments, the light emitting elements 51 are controlled by a computer unit (not shown) to receive instructions or activation signal to, for example, emit light to indicate a position of a coil arrangement 28, emit light according to a predetermined sequence, and/or emit light according to a specific color.

Figure 6:
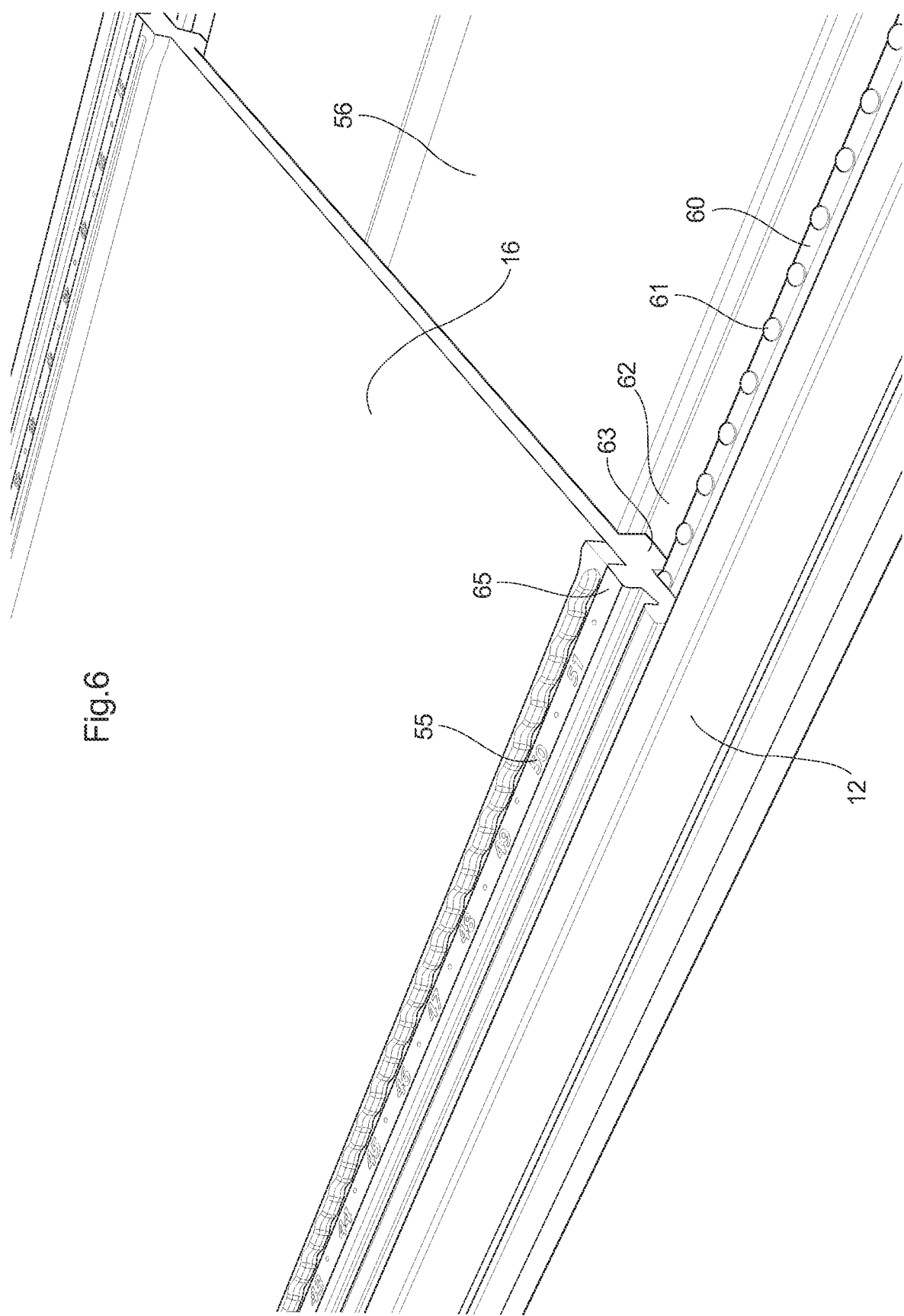
FIG. 6 shows a detailed view of another embodiment of the present invention.

With reference now to FIG. 6, a further embodiment of the present invention will be discussed. In this embodiment, position markers 55 are provided on the patient bed 16 arranged along an edge part of the patient bed 16. A position indicator 60 is arranged as an array of light emitting elements 61, in this example light emitting diodes, on upper surface 56 of the patient support 12. The array of light emitting elements 51 is arranged such that each light emitting element 51 is in line with a corresponding position marker 55 on the patient bed 16 when the bed 16 is placed in an end position or home position outside the treatment area 18 (see FIG. 3). According to this embodiment, shown in FIG. 6, the light emitting elements 51 are arranged in a guide rail 62 of the patient support 12 in which rails 63 of the patient bed 16 moves. The position markers 55 are made of a transparent or semi-transparent material or are arranged as openings or holes in an elongated part 65 of the patient bed 16. When a light emitting element 51 receives an activation signal or instructions to emit light, it will emit light towards the respective position marker 55.

Although the above description relates to embodiments that is in the light of the present knowledge considered to be the most preferable, it is clear to a person skilled in the art that the invention can be modified in many different ways within the scope defined by the appended claims.

The invention claimed is:

1. A position indicator for a system for moving a patient in a non-invasive therapy system, wherein said system for moving includes a patient support arranged outside a treatment space of a medical apparatus of the non-invasive therapy system, a treatment table arranged inside the treatment space in the medical apparatus, and a patient bed movable in a longitudinal direction from the patient support to the treatment table and back by means of activation of a transferring mechanism, wherein said position indicator comprises a number of light emitting elements arranged in said patient support and each being arranged to receive activation signals instructing a receiving light emitting element to emit light to indicate positions for treatment equipment, wherein the treatment equipment includes patient positioning devices arranged to be positioned at said patient support, wherein said light emitting elements are arranged to receive activation signals instructing the receiving light emitting element to emit light to indicate positions where said patient positioning devices should be positioned at along said patient support.

2. The position indicator according to claim 1, wherein said light emitting elements are arranged to receive activation signals instructing the receiving light emitting element to emit light to indicate positions, in a longitudinal direction, where said treatment equipment is to be positioned at said patient support.

3. The position indicator according to claim 1, wherein said patient support is provided with a number of position markers and said position indicator comprises at least one light emitting element arranged at each position marker, wherein a position marker is lit up when a corresponding light emitting element is instructed to emit light.

4. The position indicator according to claim 3, wherein said position markers includes a transparent or semi-transparent material and wherein said light emitting elements are arranged to emit light towards a respective position marker.

5. The position indicator according to claim 4, wherein said position markers are arranged on a longitudinal edge part of said patient support and wherein said light emitting elements are arranged to individually emit light towards a respective position marker.

6. The position indicator according to claim 1, wherein said light emitting elements are arranged in an upper surface of the patient support.

7. The position indicator according to claim 1, wherein said light emitting elements are arranged in a guide rail of said patient support.

8. The position indicator according to claim 1, wherein said light emitting elements are arranged to, upon receiving activation signals, emit light according to at least one of a predetermined sequence and a predetermined color.

9. The position indicator according to claim 8, wherein said light emitting elements are arranged to, upon receiving activation signals, to emit light according to a predetermined sequence and/or color, wherein a certain predetermined sequence and/or color is associated with a certain treatment equipment.

10. The position indicator according to claim 1, wherein the treatment equipment includes a coil arrangement including an anterior coil and a support stand, the support stand resting on the patient bed adjacent to longitudinal edges of said patient bed and being slidable along the patient bed in a longitudinal direction, wherein said light emitting elements are arranged to receive activation signals instructing the receiving light emitting element to emit light to indicate positions where said coil arrangement should be positioned at along said patient support.

11. A method for indicating a position in a system for moving a patient in a non-invasive therapy system, wherein said system for moving includes a patient support arranged outside a treatment space of a medical apparatus of the non-invasive therapy system, a treatment table arranged inside the treatment space in the medical apparatus, a patient bed movable in a longitudinal direction from the patient support to the treatment table and back by means of activation of a transferring mechanism, wherein said method comprises:
activating a position indicator comprising a number of light emitting elements arranged in said patient support, each being arranged to receive activation signals instructing a receiving light emitting element to emit light to indicate positions for treatment equipment, wherein the treatment equipment includes patient positioning devices arranged to be positioned at said patient support, further comprising providing activation signals to said light emitting elements instructing the receiving light emitting element to emit light to indicate positions, in a longitudinal direction, where said patient positioning devices should be positioned at said patient support.

12. The method according to claim 11, including activating a position indicator comprising a number of light emitting elements arranged in said patient support, each being arranged to receive activation signals instructing the receiving light emitting element to emit light to indicate positions, in a longitudinal direction, where said treatment equipment it is to be positioned at said patient support.

13. The method according to claim 11, wherein said patient support is provided with a number of position markers and said position indicator comprises at least one light emitting element arranged at each position marker, further comprising lightening up a position marker by instructing a corresponding light emitting element to emit light.

14. The method according to claim 13, wherein said position markers includes a transparent or semi-transparent material and are arranged on a longitudinal edge part of said patient support, further comprising individually emitting light towards a position marker from a corresponding light emitting element.

15. The method according to claim 11, further comprising providing activation signals to instruct said light emitting elements to emit light according to at least one of a predetermined sequence and a predetermined color.

16. The method according to claim 15, wherein a certain at least one of a predetermined sequence and a predetermined color is associated with a certain treatment equipment.

17. The method according to claim 11, wherein the treatment equipment includes a coil arrangement including an anterior coil and a support stand, the support stand resting on the patient bed adjacent to longitudinal edges of said patient bed and being slidable along the patient bed in a longitudinal direction, further comprising providing an activation signal to said light emitting elements instructing the receiving light emitting element to emit light to indicate positions, in a longitudinal direction, where said coil arrangement is to be positioned at said patient support.

* * * * *